United States Patent [19]

Chattha

[11] Patent Number: 4,611,047

[45] Date of Patent: Sep. 9, 1986

[54] DICARBOXYLIC ACID AZOMETHINES AND HIGH GLASS TRANSITION TEMPERATURE POLYESTER PRODUCTS PRODUCED THEREFROM

[75] Inventor: Mohinder S. Chattha, Livonia, Mich.

[73] Assignee: Ford Motor Company, Dearborne, Mich.

[21] Appl. No.: 811,861

[22] Filed: Dec. 20, 1985

Related U.S. Application Data

[62] Division of Ser. No. 712,055, Mar. 15, 1985, Pat. No. 4,595,761.

[51] Int. Cl.$^4$ ............................................. C08G 59/52
[52] U.S. Cl. ................................. 528/114; 528/107; 528/327
[58] Field of Search ......................... 528/107, 114, 327

[56] References Cited

U.S. PATENT DOCUMENTS

| | | | |
|---|---|---|---|
| 3,419,525 | 12/1968 | Aelony | 528/114 X |
| 3,516,970 | 6/1970 | Webb | 528/245 |
| 3,516,971 | 6/1970 | Webb | 528/245 |
| 3,526,611 | 9/1970 | Webb | 528/245 |
| 4,119,609 | 10/1978 | Allen et al. | 528/114 X |
| 4,129,556 | 12/1978 | Zondler et al. | 528/99 X |
| 4,160,081 | 7/1979 | Kvita et al. | 528/114 X |
| 4,367,328 | 1/1983 | Bertram et al. | 528/99 X |
| 4,410,681 | 10/1983 | Prindle | 528/99 X |

OTHER PUBLICATIONS

Synthesis and Thermal Stability of Structurally Related Aromatic Schiff Bases and Acid Amides, Delman, Stein and Simms, Macromol Sci. (Chem.) A1(1), 147–178 (1967).

*Primary Examiner*—Earl Nielsen
*Attorney, Agent, or Firm*—Lorraine S. Melotik; Roger L. May

[57] ABSTRACT

This invention is directed to acid terminated azomethines formed by reacting aromatic dialdehydes or aromatic diketones with amino-carboxylic acid compounds. These oligomers may be reacted with epoxy resins to produce polymer material having high glass transition temperatures.

9 Claims, No Drawings ized.
DICARBOXYLIC ACID AZOMETHINES AND HIGH GLASS TRANSITION TEMPERATURE POLYESTER PRODUCTS PRODUCED THEREFROM This is a division of application Ser. No. 712,055, filed Mar. 15, 1985, now U.S. Pat. No. 4,595,761.

Reference is made to concurrently filed and commonly assigned related U.S. application Ser. No. 711,881 pending, entitled "Hydroxyl Terminated Azomethines and High Glass Transition Temperature Polyether Products Produced Therefrom", to Chattha. Reference is also made to commonly assigned copending U.S. application Ser. No. 714,141, entitled "Hydroxyl Terminated Azomethines and High Glass Transition Temperature Polyether Products Produced Therefrom", filed Mar. 20, 1985 to Chattha.

TECHNICAL FIELD

This invention relates to acid terminated azomethines which may be reacted with epoxy resins to produce polymeric materials with high glass transition temperatures. Azomethines are compounds containing a ($<$C$=$N—) unit in their backbone. More particularly, this invention is directed to carboxyterminated, aromatic azomethines formed by reacting aromatic dialdehydes or aromatic diketones with particular amino-carboxylic acid compounds.

BACKGROUND OF THE INVENTION

Both low and high molecular weight azomethine polymers (commonly termed Schiff-base polymers) have been described in literature and various patents. Generally, these azomethine polymers are made by reacting aromatic dialdehydes with aromatic diamines. The preparation of low molecular weight polyazomethines by solution polymerization has been described by Delman et al in Macromol Sci. Chem. Al. (1) 147–148 (67). U.S. Pat. Nos. 3,516,970, 3,516,971 and 3,526,611 describe the synthesis by melt polymerization of high molecular weight Schiff-base polymers. The high molecular weight azomethine polymers are taught as being highly insulating and thermally stable, i.e., capable of withstanding high temperatures for sustained periods of time without undergoing significant degradation or phase change. They have thus been suggested for aerospace applications requiring polymers having high temperature stability. While the carboxy terminated azomethines of this invention are of relatively low molecular weight, we have found that they have good thermal stability and high melting points.

It is known in the art that carboxy functional materials may be reacted with epoxy resins to form thermoplastic and thermoset materials. We have now found that the carboxy terminated aromatic azomethines of this invention, when reacted with epoxy resins, produce polyester materials with high glass transition temperatures. Such high glass transition temperature polyesters would be useful in applications requiring materials having good thermal stability and relatively high melting points.

BRIEF DESCRIPTION OF THE INVENTION

This invention is directed to a carboxy terminated aromatic azomethine oligomer which has a high glass transition temperature. The azomethine is formed by reacting:

(A) aromatic compounds having the formula: ORC-X-CRO, wherein X is a phenyl group, each R is an alkyl group having 1–5 carbon atoms or, preferably, H, and the CRO groups are linked through X at the 1,3 or 1,4 positions; and (B) compounds having the formula: $H_2N$-Y-$(R')_n$-COOH, wherein Y is a phenyl or pyridine group, n=0 or 1, R' is an organic group, and the $H_2N$ group and the COOH group are linked through Y at the 1,3 or 1,4 positions, the compounds (A) and (B) being reacted in about a 1:2 molar ratio and under conditions wherein the CRO groups of (A) and the $NH_2$ group of (B) react.

This invention is also directed to the polyester products produced by reacting epoxy resins and the acid terminated aromatic azomethines described above.

Advantageously, the high melting azomethines of this invention, when reacted with epoxy resins, form high glass transition temperatures polyesters which are suitable for use as, for example high temperature adhesives, composites, and potting compounds.

DETAILED DESCRIPTION OF THE INVENTION

This invention is directed to carboxyl terminated aromatic azomethine oligomers. These azomethines, containing two carboxyl groups, are formed by reacting aromatic diketones or aromatic dialdehydes (compound A) with amine compounds having a carboxyl group (compound B) in about a 1:2 molar ratio. Each of the reactants for forming these acid terminated azomethines will be discussed in greater detail.

The aromatic diketones or aromatic dialdehydes reacted to form the acid terminated azomethines of this invention comprise compounds having the formula: ORC-X-CRO, wherein X is a phenyl group and each R is an alkyl group having 1–5 carbon atoms or H. As is well known in the art, if R is an alkyl group, this compound is an aromatic diketone or, if R is hydrogen, this compound is an aromatic dialdehyde. Preferably, R of this compound is hydrogen, since the aldehyde group is more reactive with an amine group than is the ketone group. The CRO groups are linked through X at the 1,3 or 1,4 position. These azomethines can be reacted in accordance with the invention with epoxy resins to form thermoplastic and thermosetting polyesters. Azomethines formed from compounds wherein the CRO groups are linked through the phenyl group X at the 1,3 positions, as compared to the 1,4 positions, yield polyesters having increased flexibility. On the other hand, azomethines formed from compounds wherein the CRO groups are at the 1,4 positions of X, as compared to the 1,3 positions, yield polyesters having higher glass transition temperatures. It is preferred, in order to form high glass transition temperature polyesters, to thus employ the azomethines formed from the 1,4 position compounds. Exemplary of the aromatic diketones and aromatic dialdehydes which may be employed to form the azomethines of this invention are terephthaldicarboxaldehyde, isophthaladehyde, and diacetylbenzene with terephthaldicarboxaldehyde being most preferred. Mixtures of suitable aromatic diketones and/or aromatic dialdehydes, may also be used as component (A) in forming the azomethine of this invention.

The amine compounds which are reacted with compound (A) to form the azomethines of this invention contain a terminal carboxyl group and are selected from compounds having the formula: $H_2N$-Y-$(R')_n$-COOH, wherein Y is a phenyl or pyridine group, n is 0 or 1, R' is an organic group and the $H_2N$ group and the COOH group are linked through Y at the 1,3 or 1,4 positions. The hydrogens of the phenyl or pyridine group may be substituted by non-interferring functionality. Preferably, at most, only one or two of the hydrogens of the phenyl or pyridine group are substituted. Exemplary of non-interferring functionality which may be substituted for the hydrogens of the phenyl or pyridine group, (i.e., other than at the linking positions at Y for the amine and carboxyl group) are methyl, methoxy, and chloro. When n is 0, the amine and carboxyl groups are linked directly to the phenyl or pyridine group. When n is 1, the amine group is linked directly to the phenyl or pyridine group and the carboxyl group is linked to the phenyl or pyridine group through an organic group, R'. This organic group may be any organic group which does not interfere with the reaction of the compound (A) and compound (B) according to this invention. It may be selected from a variety of organic groups including substituted or unsubstituted alkyl groups preferably having 1–5 carbon atoms such as methylene, propylene and butylene, amide, ester and ether groups. The use of the organic group in the amine compound used to form the azomethine azomethines results in increased flexibility in the polyesters formed by reacting these oligomers with epoxy resins. Linking the amine and carboxyl groups through Y at the 1,3 positions, as compared to the 1,4 positions, results in azomethines which form polyesters having increased flexibility. On the other hand, linking the amine group and the carboxyl group through Y at the 1,4 positions, results in polyesters having higher glass transition temperature. It is preferred, in order to form high glass transition temperature polyesters, to thus employ the azomethines formed from the 1,4 position compounds. Amine-carboxylic acid compounds which may be employed to form the azomethines of this invention include, but are not limited to, p-aminobenzoic acid, m-aminobenzoic acid, p-aminohippuric acid, 3-amino-4-methoxybenzoic acid, 3-amino-4-methylbenzoic acid, 4-amino-3-methylbenzoic acid, p-aminophenyl acetic acid, 6-aminonicotinic acid, 6-aminohexanoic acid, and 4'-aminooxanilic acid. As would be apparent to those skilled in the art, mixtures of the amino-carboxylic acid compounds may also be employed as component (B) in this invention.

In forming the oligomers of this invention, compound (A) and compound (B) are reacted in about a 1:2 molar ratio under conditions wherein the CRO groups of compound (A) and the amine group of compound (B) react. By reacting compound (A) and compound (B) in about a 1:2 molar ratio, all of the CRO groups will be reacted. While it is not generally necessary, compound (B) may be employed in the reaction mixture in a slight excess of this ratio, e.g., in about 1:2–2.2 molar ratio, so as to insure that compound (A) and compound (B) are reacted in about 1:2 molar ratio and thus all of the CRO groups of compound (A) will be reacted.

Exemplary of one embodiment of this invention comprises the azomethine formed by the reaction of terephthaldicarboxaldehyde with p-aminobenzoic acid, as shown in the following equation:

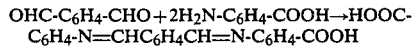

OHC-$C_6H_4$-CHO + 2$H_2N$-$C_6H_4$-COOH → HOOC-$C_6H_4$-N=CH$C_6H_4$CH=N-$C_6H_4$-COOH

Generally in forming the oligomer, the compounds are dissolved separately in suitable solvents and then the solutions are mixed and heated to an elevated temperature, generally between about 90°–200° C., more preferably between about 170°–200° C., whereafter the compounds react to form the oligomer. This azomethine product generally separates out in a crystalline form which can be easily recovered from the solvent. Exemplary of solvents which may be employed for making the azomethine in this manner include ethanol, acetone, dimethyl formamide and dimethyl acetamide. Catalysts, while not generally being required to catalyze this reaction, particularly when employing dialdehydes as component (A), may be employed. Exemplary of such catalysts are p-toluene sulfonic acid, phosphoric acid and sulfuric acid.

While the above procedure describes a method for making the azomethine, its description is not meant to be limiting to the oligomer of this invention and selection of a method to produce the azomethines of this invention from components (A) and (B) would be well within the skill of those in the art.

The oligomers of this invention are particularly useful in making high glass transition temperature polyester products such as adhesives, composites, and potting compounds, by reacting the azomethines with epoxy resins. If the azomethines of this invention are reacted with diepoxide materials, high glass transition temperature thermoplastic polyesters are formed. When reacted with epoxies having more than two epoxide groups per molecule, the dicarboxylic acid azomethines of this invention produce high glass transition temperature thermosets. Epoxy resins which may be reacted with the dicarboxylic acid azomethines of this invention include, but are not limited to, those having, on average, two or more epoxide groups per molecule. A large number of such polyepoxide resins are known to those skilled in the art. Exemplary of such polyepoxide resins are those derived from a dihydric phenol or dihydric alcohol and an epihalohydrin. Examples of epihalohydrins are epichlorohydrin, epibromohydrin and epiiodohydrin with epichlorohydrin being preferred. Dihydric phenols and dihydric alcohols are exemplified by resorcinol, hydroquinone, Bisphenol A, p,p'-dihydroxy benzol phenone, p,p'-dihydroxy phenyl, p,p'-dihydroxy diphenyl ethane, bis-(2-hydroxy naphtha) methane, 1,5-dihydroxy naphthaline, ethylene glycol, propylene glycol, 1,4-butane diol, hydrogenated Bisphenol A, 1,4-cyclohexane diol, 1,3-cyclopentane diol, cyclohexane dimethanol, and the like. These polyepoxide resins, as is well known in the art, are made in the desired molecular weights by reacting the epihalohydrin and the diols in various ratios, or by reacting a dihydric phenol with a lower molecular weight polyepoxide resin. Other polyepoxide resins are the glycidyl polyethers of Bisphenol A. Examples of commercially available epoxy resins of the type described above and useful in this invention to form, e.g., composites, include Epon 828, available from and a trademark of Shell Chemical Company (Houston, Tex.). Mixtures of the epoxy resins may also be employed as the epoxy resin reacted with the dicarboxyl azomethines to form the polyesters of this invention. While some polyepoxide resins have been discussed as exemplary for use in forming the polyester product of this invention, their disclosure is not to be considered limiting to the epoxy resin. Other epoxides will be apparent to those skilled in the art. Generally, in forming the polyester resins of this invention, the epoxy resin and the azomethine of this invention are reacted in about a 1–5:1 ratio of epoxide to acid groups, more preferably in about a 1-2:1 ratio of epoxide to acid group. However, this ratio is not meant to be limiting to this invention. The optimal ratio would depend on the application and type of composition being formed and selection of such a ratio would be within the skill of one in the art. The epoxy resin and azomethine may be reacted by any number of conventional techniques for such reactions, which optimal technique would be dependant on the particular reactants and product formed. For example, the azomethine and epoxy resin may be simply mixed together and heated to react the materials and form the polyester. Another technique comprises reacting the azomethine and epoxy resin in solvent at elevated temperatures to form the polyester product.

The invention will be further understood by referring to the following detailed examples. It should be understood that the specific examples are presented by way of illustration and not by way of limitation.

EXAMPLE 1

Terephthaldicarboxaldehyde (13.4 g) is dissolved in 100 ml ethanol and 15 ml dimethylformamide. In a separate flask 27.4 g p-amino benzoic acid is dissolved in 100 ml ethanol and 15 ml dimethylformamide. Both the above solutions are mixed at 50° C.; yellow color appears immediately and within a few minutes the product separates as light yellow crystals. The product does not melt up to 320° C.

The above diacid (1.5 g) is mixed with 7.8 g of triglycidyl p-aminophenol (Araldite MY0500, Ciba-Geigy). The reaction mixture is heated, with continuous stirring, to obtain a homogeneous mixture. The mixture is poured into an aluminum dish and is heated at 170° C. for one hour. The cured sample shows softening point of 240° C. (duPont 943 Thermal Mechanical Analyzer).

EXAMPLE 2

One gram of the diacid from Example 1 is mixed with 1.9 g of bisphenol-A diglycidyl ether in an aluminum pan. The mixture is heated on a hot plate with continuous stirring to obtain a homogeneous solution and is placed in an oven at 170° C. for one hour. The softening point of the sample is determined to be 159° C.

EXAMPLE 3

The procedure described in Example 2 is followed to prepare a cured sample from 1 g of the diacid and 2.6 g of the epoxy used therein. The softening point of the sample is found to be 133° C.

EXAMPLE 4

The sample preparation described in Example 1 is repeated by employing 1 g of the diacid and 6.8 g of the epoxy. The softening point of the cured sample is 195° C. In thermal gravimetric analysis the sample retains 38% of its weight up to 600° C.

EXAMPLE 5

Four grams of tetraglycidyl-4,4'-diaminodiphenyl methane (Araldite MY720, Ciba-Geigy) and 1 g of diacid from Example 1 are taken up in 20 g dimethylformamide and the mixture is heated with stirring to obtain a homogeneous solution. The solution is poured portion-wise into an aluminum pan and the solvent is evaporated. The residue is heated at 170° C. for one hour. The softening point of the sample is 224° C.

EXAMPLE 6

Terephthaldicarboxaldehyde (13.4 g) is dissolved in 125 ml ethanol and 12 ml dimethylformamide. In a separate flask 30.2 g p-aminophenylacetic acid is dissolved in 150 ml ethanol. Both the above solutions are mixed at 50° C.; yellow crystals appear immediately. The product is obtained as light yellow crystals by filteration.

One gram of this diacid and 1.4 g of bis-phenol-A diglycidyl ether are heated in an aluminum pan to obtain a homogeneous solution and the pan is then placed in an oven at 170° C. for one hour. The cured sample shows softening at 137° C.

EXAMPLE 7

One gram of the diacid from Example 6 and 4.5 g of triglycidyl p-aminophenol are heated in an aluminum pan, with stirring to obtain a homogeneous solution. The pan is then placed in an oven at 170° C. for one hour. The cured sample has a softening point of 212° C.

EXAMPLE 8

One gram of the diacid from Example 6 and 3.7 g of tetraglycidyl-4,4'-diaminodiphenyl methane are taken up in 25 ml dimethylforamide and the mixture is heated with stirring to obtain a homogneeous solution. The solution is drawn on a steel panel and is placed in an air flow oven at 60° C. for 15 minutes and then at 170° C. for 45 minutes. The resulting coating exhibits excellent hardness, adhesion and resistance to organic solvents.

EXAMPLE 9

Diacid azomethine is prepared from m-aminobenzoic acid as described in Example 1 instead of p-aminobenzoic acid used therein.

The above diacid (1.3 g) is mixed with 5.8 g of triglycidyl p-aminophenol and the sample is prepared as described in Example 1. The softening point of the sample is 223° C.

EXAMPLE 10

The procedure described in Example 1 is followed to prepare a diazomethine diacid from 13.4 g of terephaldicarboxaldehyde and 27.6 g 6-aminonicotinic acid.

Two grams of the above acid are mixed with 4 g of bisphenol-A diglycidyl ether and the mixture is heated to obtain a homogeneous solution. The solution is placed in an aluminum pan and is heated at 170° C. for one hour. The cured sample has softening point of 142° C.

EXAMPLE 11

1,4-diacetylbenzene (8.1 g) and p-aminobenzoic acid (13.7 g) are taken up in 150 ml dimethylformamide and 50 ml toluene. Phosphoric acid (0.25 g) is added to the above mixture and it is refluxed under Dean-Stark water separator for six hours. The product separates as yellow crystals and is filtered and dried.

One gram of the above product and 4.6 g of triglycidyl p-aminophenol are heated in an aluminum pan, with continuous stirring, to obtain a homogeneous mixture. The sample is then placed at 170° C. for one hour. The softening point of the cured material is 197° C.

While particular embodiments of the invention have been described, it will be obvious to those skilled in the art that various changes and modifications may be made without departing from the invention, and it is intended to cover in the appended claims all such modifications and equivalents as fall within the true spirit and scope of this invention.

I claim:

1. Polyester products having high glass temperatures and being formed by reacting:
   I. epoxy resin, and
   II. carboxy terminated aromatic azomethines formed by reacting:
      (A) aromatic compounds having the formula:

ORC-X-CRO, wherein X is a phenyl group, each R is H or an alkyl group having 1–5 carbon atoms, and the CRO groups are linked through X at the 1,3 or 1,4 positions; and
      (B) compounds having the formula $H_2N\text{-}Y\text{-}(R')_n\text{-}COOH$:

wherein Y is a phenyl or pyridine group, n is 0 or 1, R' is an organic group, and the $H_2N$ and COOH groups are linked through Y at the 1,3 or 1,4 positions,
   said compounds (A) and (B) being reacted in about a 1:2 molar ratio and under conditions wherein said CRO groups of (A) and said $NH_2$ group of (B) react.

2. Polyester products according to claim 1, wherein epoxy resin is selected from diepoxide resins.

3. Polyester products according to claim 1, wherein said epoxy resin is selected from epoxy resins having, on average, at least three epoxide groups per molecule.

4. Polyester products according to claim 1, wherein said R of said aromatic compounds (A) is hydrogen.

5. Polyester products according to claim 1, wherein said CRO groups are linked through X at the 1,4 positions.

6. Polyester products according to claim 1, wherein said organic group R' is selected from the group consisting of $C_1$–$C_5$ alkyl groups.

7. Polyester products according to claim 6, wherein said alkyl group is substituted with non-interfering functionality.

8. Polyester products according to claim 1, wherein at most two hydrogens of said phenyl or pyridine group of compound (B) are substituted by non-interferring functionality.

9. Polyester products according to claim 1, wherein the $H_2N$ group and the COOH group are linked through Y at the 1,4 positions.

* * * * *